US006248322B1

(12) United States Patent
Klein et al.

(10) Patent No.: US 6,248,322 B1
(45) Date of Patent: Jun. 19, 2001

(54) ATTENUATED VACCINE FOR *BLASTOMYCES DERMATITIDIS*

(75) Inventors: Bruce S. Klein; Theodore T. Brandhorst; Marcel Wüthrich, all of Madison, WI (US)

(73) Assignee: Wisconsin Alumni Research Foundation, Madison, WI (US)

( * ) Notice: Subject to any disclaimer, the term of this patent is extended or adjusted under 35 U.S.C. 154(b) by 0 days.

(21) Appl. No.: 09/551,167

(22) Filed: Apr. 17, 2000

(51) Int. Cl.[7] ................................................. A01N 63/04
(52) U.S. Cl. ................ 424/93.5; 424/184.1; 424/274.1; 424/93.1; 424/93.2; 424/93.21; 435/471; 435/254.1; 435/911
(58) Field of Search .............................. 424/184.1, 192.1, 424/274.1, 93.1, 93.2, 93.21, 93.5; 435/471, 254.1, 911

(56) References Cited

U.S. PATENT DOCUMENTS 5,093,118   3/1992   Klein et al. .
5,302,530   4/1994   Klein et al. .
5,948,413 * 9/2000   Mendoza .

OTHER PUBLICATIONS

Reiss et al. Dermatologica 152=16–22, 1976.*
T. Brandhorst et al., Targeted Gene Disruption Reveals An Adhesin Indispensable For Pathogenicity of *Blastomyces Dermatitidis*, 189 J. Exp. Med. 1207–1216 (Apr. 19, 1999—not prior art).
B. Klein et al. Altered Expression Of The Surface Protein WI–1 In Genetically Related Strains Of *Blastomyces Dermatitidis* That Differ In Virulence Regulates Recognition Of Yeasts By Human Macrophages, 62 Infect. Immun. 3536–3542 (1994).
L. Hogan et al., Transforming DNA Integrates At Multiple Sites In The Dimorphic Fungal Pathogen *Blastomyces Dermatitidis*, 186 Gene 219–226 (1997).
L. Hogan et al., Genomic Cloning, Characterization, And Functional Analysis Of The Major Surface Adhesin WI–1 On *Blastomyces Dermatitidis* Yeasts, 270 J. Biol. Chem. 30725–30732 (1995).
P. Worsham et al., Quantitative Plating Of Histoplasma Capsulatum Without Addition Of Conditioned Medium Or Siderophores, 26 J. Vet. Med. Mycol. 137–143 (1988).

S. Lyons et al., An Immunological Method For Detecting Gene Expression In Yeast Colonies, 81 PNAS USA 7426–7430 (1984).
B. Klein et al., Purification And Characterization Of the Major Antigen WI–1 From *Blastomyces Dermatitidis* Yeasts, And Immunological Comparison With A Antigen, 62 Infect. Immun. 3890–3900 (1994).
S. Newman et al., The WI–1 Antigen On *Blastomyces Dermatitidis* Yeasts Mediates Binding To Human Macrophase CD18 and CD14 Receptors, 154 J. Immunol. 753–761 (1995).
J. Chan et al., Killing Of Virulent Mycobacterium Tuberculosis By Reactive Introgen Intermediates Prodced By Activated Murine Macrophages, 175 J. Exp. Med. 1111–1122 (1992).
J. Mukherjee et al., Therapeutic Efficacy Of Monoclonal Antibodies To Cryptococcus Neoformans Glucuronoxylomnnan Alone And In Combination With Amphotericin B., 38 Antimicrob. Agents Chemother. 580–587 (1994).
S. Zebedee et al., Mouse–Human Immunoglobulin G1 Chimeric Antibodies With Activities Against Cryptococcus Neoformans, 38 Antimicrob. Agents Chemother. 1507–1514 (1994).
J. Mukherjee et al., Antibodies To Crytococcus Neoformans Glucuronoxylomannan Enhance Antifungal Activity Of Murine Macrophages, 63 Infect. Immune. 573–579 (1995).
M. Riesselman et al., Improvements And Important Considerations Of An Ex Vivo Assay To Study Candida Albicans–Splenic Tissue Interactions, 145 J. Immunol. Meth. 153–160 (1991).
M. Wüthrich et al., Immunogenicity And Protective Efficacy Of The WI–1 Adhesin Of *Blastomyces Dermatitidis*, 66 Infect. Immun. 5443–5449 (1998).
Gudding et al., Vaccination Of Cattle Against Ringworm Caused By *Trichophyton Verrucosum*, 47 Am. J. Vet. Res., 2415–2417 (1986).
L. Romani et al., Course Of Primary Candidiasis In T Cell–Depleted Mice Infected With Attenuated Variant Cells, 166 J. Infect. Dis. 1384–1392 (1992).

* cited by examiner

*Primary Examiner*—Donna C. Wortman
*Assistant Examiner*—Robert A. Zeman
(74) *Attorney, Agent, or Firm*—Quarles & Brady LLP

(57) ABSTRACT

Disclosed herein are attenuated forms of the *B. dermatitidis* fungus. The fungus remains replication competent but is unable to express the WI-1 protein. One can administer this fungus to a dog, human, or other mammal to vaccinate them against the wild type fungus. Preferably, the administration is by subcutaneous injection.

5 Claims, No Drawings

ATTENUATED VACCINE FOR *BLASTOMYCES DERMATITIDIS*

CROSS REFERENCES TO RELATED APPLICATIONS

Not applicable.

STATEMENT REGARDING FEDERALLY SPONSORED RESEARCH

This invention was made with United States government support awarded by the following agency: NIH AI40996. The United States has certain rights in this invention.

BACKGROUND OF THE INVENTION

The present invention relates to attenuated variants of the fungus *B. dermatitidis*, and methods of using them to vaccinate against the wild type fungus.

Blastomycosis is a disease caused by infection with the fungus *Blastomyces dermatitidis*. Humans and other animals (particularly dogs) can be infected by inhaling aerosolized fungal spores from, for example, soil where the organism dwells. At body temperature, these spores convert to yeast forms. Acute primary pulmonary infection caused by the yeast can produce an influenza or pneumonia syndrome. Progressive forms of the disease can cause serious damage to the lungs, skin, bones, joints, or prostate gland.

It is therefore desirable to develop a vaccine against this disease. In U.S. Pat. No. 5,093,118 (the disclosure of this patent and all other publications referred to herein being incorporated by reference as if fully set forth herein) we described the isolation of a cell wall protein of the fungus *B. dermatitidis* that we named WI-1. It was suggested that this protein be used in a vaccine for Blastomycosis.

In U.S. Pat. No. 5,302,530 we described the coding DNA for this protein. While WI-1 has been of some value in raising antigenic responses, its impact on long-term survival of hosts challenged with certain strains of the wild type fungus has not been sufficient. Thus, efforts have continued to try to find more widely effective vaccines against this disease.

In unrelated work, fluorescence staining of the fungal surface and extractions of cell wall proteins have shown that WI-1 can be expressed to a lower extent in genetically related strains having higher virulence. B. Klein et al., 62 Infect. Immun. 3536–3542 (1994). If anything, this would have taught away from trying to delete WI-1 expression as a means of attenuating a fungus.

It should also be noted that we recently published techniques for genetically manipulating *B. dermatitidlis* by using DNA mediated gene transfer. See L. Hogan et al., 186 Gene 219–226 (1997).

To date we are unaware of anyone having successfully obtained an attenuated replication competent *B. dermatitidis* fungal vaccine, or any other vaccine against this fungus (e.g. protein based, DNA based, or otherwise) which meets the needs in this art. Thus, a need exists for an improved vaccine against *B. dermatitidis*.

BRIEF SUMMARY OF THE INVENTION

In one aspect the invention provides a recombinant, replication competent, *B. dermatitidis* fungus that is incapable of expressing WI-1 protein. Preferably the fungus does not contain any portion of the WI-1 coding gene.

In another aspect the invention provides a method for causing a mammal to resist lung infection by *B. derrmatitidis*. One administers to the mammal the above recombinant fungus. Preferably, the mammal is canine or human, and the administration is by subcutaneous injection on multiple days.

Strains of *B. dermatitidis* have been modified to render them incapable of expressing a WI-1 protein. They are otherwise intact. Particularly with respect to subcutaneous injection on multiple days, hosts exposed to our attenuated fungus develop infection resistance against the wild type fungus.

Particularly surprising is that dosages can be provided which are high enough to provide infection resistance and increased long-term survival, but low enough so that the attenuated fungus does not reside throughout the body on a long-term basis. This is highly desirable.

These and other advantages of the present invention will become apparent after study of the following specification and claims.

DETAILED DESCRIPTION OF THE PREFERRED EMBODIMENTS

A. General Overview.

Our general approach was to cross out, via genetic recombination, the coding DNA for WI-1. Apart from inserting an antibiotic resistance marker we left the rest of the fungus DNA intact. Our gene targeting efforts capitalized on the preferred fate of incoming DNA in *B. dermatitidis*, which is integrative transformation. Substantial WI-1 DNA flanking the hph selectable marker Lwas used to target the knockout vector pQWhph and achieve the desired crossover event.

WI-1 was disrupted by allelic replacement in both ATCC strains 26199 and 60915. In each positive candidate, strains #55 and #99, the amplified joint fragment was 675 bp.

B. Fungal Strains and Plasmids.

Blastomyces dermatitidis American Type Culture Collection (ATCC) strains 26199 and 60915 were used as two examples of the wild type strain. Wild-type, parental strain 26199 was isolated originally from a human patient and is highly virulent. The genetically related strain 60915 was derived after repeated passage of strain 26199.

C. Attenuation of Fungus.

The targeting vector pQWhph (see FIG. 1A of T. Brandhorst et al. 189 J. Exp. Med. 1207–1215 (Apr. 19, 1999)) was constructed as follows. pQE32/WI-1 (8.3 kb) was derived from a Qiagen expression vector pQE32 (3.5 kb) and an AccIII fragment of the genomic WI-1 gene (4.8 kb). See B. Hogan et al., 270 J. Biol. Chem. 30725–30732 (1995) A BamH1 site in the 3' UTR of WI-1 was removed by HinD III digestion and religation. Another BamH1 site in the 5' UTR was removed by EcoRI-NruI deletion. The resulting plasmid, pQWΔΔ, was digested with BamH1 to excise 1.4 kB of WI-1 coding sequence. A 1.4 kB hph cassette (*E. coli* hph driven by 375 bp of WI-1 upstream sequence) was amplified from pWI-1P (see L. Hogan et al., 186 Gene 219–226 (1997)) using PCR primers TB#1 (SEQ ID NO. 1) and TB#2 (SEQ ID NO. 2), which added BamH1 sites.

The hph cassette was ligated into the pQWΔΔ BamHI-digested vector, which was then linearized with HinD III, and the 1.4 kb HinD III fragment containing the 3'-untranslated region of WI-1 was ligated back into place. The orientations of the hph cassette and the HinD III fragment were verified by restriction analysis.

pCB1528, containing the sulfonyl urea resistance gene of *Magneportha grisea*, was generously provided by Drs. James Sweigard (Dupont, Wilmington, Del.) and Paul Szaniszlo (University of Texas, Austin), and used for reconstitution of WI-1 in knockout strains.

D. Growth of Fungi

*Blastomyces dermatitidis* was maintained in the yeast form by growth on Middlebrook 7H10 agar medium containing oleic acid-albumin complex (OADC; Sigma Chemical Co., St. Louis, Mo.). Liquid cultures of yeast were grown in Histoplasma macrophage medium (HMM) (P. Worsham et al., 26 J. Vet. Med. Mycol. 137–143 (1988)) on a rotary shaker at 200 rpm. All cultures were maintained at 37° C.

To measure the growth rate of yeasts, cells were grown synchronously in HMM and inoculated at a concentration of $2\times10^4$ per ml into 50 ml of fresh medium. Cultures were incubated at 37° C. on a rotary shaker at 200 rpm for 72 hours. Growth rates were monitored every 24 hours by both haemocytometer cell count and OD600.

E. Replacement of WI-1 Gene.

*Blastomyces dermatitidis* yeast cells of strains 26199 and 60915 were transformed with 5 $\mu$g to 10 $\mu$g of Xba I-linearized pQWhph, using electroporation conditions analogous to those previously described in L. Hogan et al., 186 Gene 219–226 (1997). Transformants were selected on HMM agar containing 200 $\mu$g/ml of hygromycin B. Replicates plated onto nitrocellulose membranes overlaying brain heart infusion (BHI) agar (Difco laboratories, Detroit, Mich.) were lysed with 0.2 M NaOH, 0.1% SDS and 0.5% mercaptoethanol analogous to the procedures described in S. Lyons et al., 81 PNAS USA 7426–7430 (1984). Membranes were probed with pooled anti-WI-1 monoclonal antibodies (mAb) DD5-CB4, AD3-BD6, BD6-BC4, and CA5-AA3 (see generally B. Klein et al., 62 Infect. Immun. 3890–3900 (1994)) (hybridomas were generously provided by Drs. Errol Reiss and Christine Morrison, Centers for Disease Control, Atlanta, Ga.) using standard immunoblotting techniques.

The multinucleate nature of *B. dermatitidis* yeast had to be addressed to isolate cells with a WI-1 negative phenotype, as the presence of heterologous, "silent" nuclei might allow phenotypic reversion. To obtain genetic homogeneity at the WI-1 locus, each candidate isolate was taken through several rounds of single-cell isolation on selective medium with resultant colonies re-screened as above. This protocol has been shown to render transformants of multinucleate fungi homogenous for altered genes.

Resulting candidates were screened for evidence of gene replacement by PCR. Primers internal to the WI-1 gene were used to determine if candidates contained an intact WI-1 locus. If an intact locus was not detectable, homologous recombination was assessed by amplifying the junction between the transformed hph gene and sequences 5' to the WI-1 promoter (not on the transforming vector). Primers were SEQ ID NO. 3 (forward) and SEQ ID NO. 4 (reverse). Knockouts were confirmed by Southern analysis.

F. Detection of WI-1 Protein and DNA

The presence of WI-1 protein was assayed by immunofluorescence staining, SDS-PAGE, and Western blotting. Immunofluorescence staining was performed as described L. Hogan et al., 270 J. Biol. Chem. 30725–30732 (1995); S. Newman et al., 154 J. Immunol. 753–761 (1995); and B. Klein et al., 62 Infect. Immun. 3536–3542 (1994). Briefly, yeast ($10^6$ cells) were stained for WI-1 indirectly using 1 $\mu$g anti-WI-1 mAb DD5-CB4 followed by goat anti-mouse IgG-FITC.

Stained cells were inspected for fluorescence microscopically using an Olympus BX60 fluorescent microscope or a FACScan flow cytometer (Becton Dickinson, San Jose, Calif.). Cell-associated proteins were extracted by boiling yeast in treatment buffer containing 1.5% SDS, and 5.0% 2-mercaptoethanol for 3 to 5 min, followed by analysis of the cell-free material by SDS-PAGE and Western blotting using anti-WI-1 mAb DD5-CB4 as described in L. Hogan et al., 270 J. Biol. Chem. 30725–30732 (1995).

For Southern analysis, chromosomal DNA was prepared by grinding cells in liquid nitrogen and extracting them in detergent as described in L. Hogan et al., 186 Gene 219–226 (1997). Purified DNA was restricted with Xba I (Promega, Madison, Wis.) at a ratio of 40 units per 10 $\mu$g of DNA, incubated at 37° C. overnight, and then separated on 1% Agarose gel and transferred to nitrocellulose membrane.

A 100 ng aliquot of probe was labeled with $\alpha[^{32}P]$ dCTP to a specific activity of $10^9$ cpm/$\mu$g using random oligonucleotides as primers (Pharmacia, Piscataway, N.J.). Washed Southern blots were used to expose Kodak XAR-5 film with intensifying screens at −80° C.

G. Assays

Murine macrophage cell line J774.16 [see generally J. Chan et al., 175 J. Exp. Med. 1111–1122 (1992); J. Mukherjee et al., 38 Antimicrob. Agents Chemother. 580–587 (1994); S. Zebedee et al., 38 Antimicrob. Agents Chemother. 1507–1514 (1994); J. Mukherjee et al., 63 Infect. Immune 573–579 (1995)], generously provided by Dr. Arturo Casadevall (Yeshiva University, NY), was used in most in vitro binding and phagocytosis assays. Further experiments were done with resident peritoneal macrophages of BALB/c mice.

Macrophages were grown in Dulbeccos Modified Eagle medium (Gibco Laboratories, Life Technologies, Inc., Grand Island, N.Y.) with 10% heat-inactivated fetal calf serum (HyClone Laboratories Inc., Logan, Utah), 10% NCTC-109 medium and 1% nonessential amino acids (Gibco BRL), and plated at $2.5\times10^4$ cells per well in 16-well tissue culture Chamber Slides (Nunc Inc., Naperville, Ill.). Cells were stimulated with 500 U per ml of recombinant murine gamma interferon (IFN-$\gamma$ Boehringer Mannheim, Germany). After overnight incubation at 37° C./8% $CO_2$, medium in each well was replaced with fresh medium containing 500 U of IFN-$\gamma$/ml, 3 $\mu$g per ml of lipopolysaccharide (LPS; Sigma) and *B. dermatitidis* yeasts.

Binding and phagocytosis of yeasts was analyzed in vitro as described in J. Chan et al., 175 J. Exp. Med. 1111–1122 (1992); J. Mukherjee et al., 38 Antimicrob. Agents Chemother. 580–587 (1994); S. Zebedee et al., 38 Antimicrob. Agents Chemother. 1507–1514 (1994); and J. Mukherjee et al., 63 Infect. Immune 573–579 (1995). Briefly, yeasts were heat-killed for 45 min at 65° C. and stained with rhodamine isothiocyanate (RITC) (10 $\mu$g/ml). Assays done in the presence and absence of complement employed 10% normal mouse serum (NMS) and heat-inactivated NMS, respectively.

Complement was inactivated by heating NMS at 56° C. for 30 min. Yeasts and macrophages were incubated at an effector-to-target ratio of 1:4 for varying periods at 37° C./8% $CO_2$. Unattached yeasts were removed by washing wells thrice with phosphate-buffered saline. Attached but undigested yeasts were stained with 0.1% Uvitex 2B (Specialty Chemicals for Medical Diagnostics, Kandern, Germany) for 30 seconds. Cells were fixed in 1% paraformaldehyde for 15 min. After fixation, glycerol was added to the slide. To quantify binding and phagocytosis, the number of yeasts attached to and ingested by 100 macrophages was counted at 1000× magnification using a U-MWU fluorescence cube in an Olympus BX60 microscope (Leeds Precision Instruments, Inc. Minneapolis Minn.).

Binding of yeast to lung tissue was analyzed using modifications to an ex vivo assay described in M. Riesselman et al., 145 J. Immunol. Meth. 153–160 (1991). Lung tissue from a healthy mouse was embedded in O.C.T.

compound (Miles Inc., Elkhart, Ind.), frozen in liquid isopentane at −80° C., and sliced into thin, 6-μm sections in a cryostat at −20° C. Sections were applied to Superfast/plus®-coated glass slides (Fisherbrand, Fisher Scientific, Itasca, Ill.) and air dried. RITC-stained yeasts ($1\times10^6$) in 0.1 ml Hanks balanced salt solution (HBSS) containing 20 mM Hepes, 0.25% bovine serum albumin and 3 mM $CaCl_2$, were added to a wax-inscribed circle of the tissue section.

Slides were incubated for 60 min. at 37° C., washed thrice with HBSS to remove unattached yeasts, and fixed with 1.25% glutaraldehyde for 35 min at room temperature. Binding of yeasts was enumerated by counting the number that adhered to a 0.01 $mm_2$ area of the slide, viewed at 600× magnification using an Olympus IX50 fluorescent microscope (Leeds Precision Instruments). Results are expressed as the mean±SEM of at least six experiments.

H. Model of Infection

Male BALB/c mice approximately 5–6 weeks of age (Harlan Sprague Dawley, Madison, Wis.) were infected with *B. dermatitidis* yeasts intranasally as described in M. Wuthrich et al., 66 Infect. Immun. 5443–5449 (1998). Briefly, mice were anesthetized with inhaled Metafane® (Mallinckrodt Veterinary Inc., Mundelein Ill.) to administer a 25-μl suspension of yeast cells dropwise into their nares. The minimum number of yeasts needed to achieve a lethal infection was established in preliminary work as $10^2$ yeasts intranasally for ATCC 26199, and $10^6$ yeast for ATCC 60915.

I. Results of Recombinant Fungal Formation

The phenotype and genotype of the knockouts were established by anti-WI-1 mAb fluorescence staining, Western blots of extracted protein, and Southern analysis. Surface WI-1 was not detectable on knockout strain #55 either by FACS analysis or Western blotting of extracted cell wall proteins. Similar results were observed in isogenic strains ATCC 60915 and knockout #99.

Southern analysis of reconstituted strain #4/55 demonstrated that the WI-1 transgene was located on a single Xba I fragment that differed in size from the retained 8.3 kB fragment harboring an hph-disrupted copy of WI-1 (FIG. 2C). This indicated that the WI-1 transgene had integrated ectopically, rather than homologously, into the chromosome in a single copy.

Thus, phenotypic and genotypic analyses demonstrated that isogenic strains differing in the expression of WI-1 had been created: wild-type parental strain 26199 with a high level of expression, strain #55 devoid of WI-1, and stain #4/55 with expression restored to the level of wild-type, or perhaps higher. In addition, parental strain 60915 containing WI-1 and its isogenic knockout strain, #99, lacking WI-1 were also developed.

J. Vaccination Protocols.

Mice were immunized with either $10^5$ live or dead #55 yeast twice two weeks apart by the subcutaneous route and challenged two weeks after the boost with an intranasal injection of $10^4$ wild type 26199 yeasts. The preferable sites for subcutaneous injection are half the dose dorsal and the other half at the base of the tail. Four weeks later, mice were sacrificed and analyzed for their burden of lung infection. Lung colony forming units ("CFU") of the wild type fungus were calculated as the geometric mean of nine mice per group. Untreated mice showed lung CFU of 113,505, dead recombinant yeast showed 3,563 CFU, and our recombinant fungus showed 112. Thus, our recombinant fungus led to a substantial decrease in wild type infection.

Similar experiments were conducted comparing the effect of a single immunization with multiple immunizations. We found a marked increase in the effectiveness of the vaccine by providing multiple injections spaced over time as compared to a single injection.

We also determined that when injection dosages of the recombinant fungus were kept below $10^7$ CFU, subcutaneous injection sites were an optimal location for injection because six weeks after the injection none of the recombinant fungus was in the lung. Thus, our recombinant is a fungus capable of being readily cleared from the body.

Still other of our experiments have analyzed the survival rates of mice that have been vaccinated and challenged by the wild type fungus. Absent the vaccine the typical survival for a challenged mouse was less than thirty days. With the recombinant fungus vaccine, 100% survived more than thirty days.

We also ran an experiment determining that a vaccine derived from one parental strain provided cross protection against a different *B. dermatitidis* strain. This is an important feature rendering the vaccine more commercially useful.

We also determined that subcutaneous vaccination was preferable when compared to intranasal routes. This is surprising as blastomycosis is a lung focused disease. It would have been expected that administration directly to the lungs would have been superior. In this regard, our experiments have established that survival percentage beyond 120 days in mice is increased by about 30% by using multiple subcutaneous administrations when compared to an administration of intranasal, followed by subcutaneous, followed by intravenous administration.

Optimal dosages for a mouse appear to be roughly $2\times10^5$ colony forming units, administered twice two weeks apart. For other size mammals (e.g. humans; dogs) one would increase the dosage to about $7\times10^5$ per kg of body weight.

We are currently conducting experiments with dogs. Thus far we have not noticed any significant adverse side effects in either mice or dogs. For dogs, we have injected the yeast subcutaneously at the back of the neck. For humans we would preferably use an injection site located in the arm.

While many different types of injection carriers may be suitable, we prefer to dissolve our colony forming units in PBS (phosphate buffered saline).

While specific embodiments have been described above, it will be appreciated that modifications in the specific embodiments can be made within the scope of the intended invention. For example, while Applicants have deleted the entire coding region for WI-1, the fungus could be rendered WI-1 incompetent by deleting only a portion of the coding region, or by other techniques. Also, still other parental *B. dermatitidis* strains may be modified in a similar fashion. Thus, the claims should be looked to in order to judge the full scope of the invention.

INDUSTRIAL APPLICABILITY

The present invention provides a recombinant fungus suitable for use as a vaccine, and methods of using it for that purpose.

We claim:

1. A recombinant, replication competent, *B. dermatitidis* fungus that is incapable of expressing WI-1 *B. dermatitidis* protein.

2. A method of causing a live mammal to resist lung infection by *B. dermatitidis*, comprising:

administering to the mammal a recombinant fungus of claim 1.

3. The method of claim 2, wherein the mammal is selected from the group consisting of canine and human.

4. The method of claim 2, wherein the recombinant fungus is administered to the mammal by subcutaneous injection.

5. The method of claim 4, wherein the recombinant fungus is administered to the mammal by subcutaneous injection of the recombinant fungus on multiple days.

* * * * *

SEQUENCE LISTING

<160> NUMBER OF SEQ ID NOS: 4

<210> SEQ ID NO 1
<211> LENGTH: 30
<212> TYPE: DNA
<213> ORGANISM: Artificial Sequence
<220> FEATURE:
<223> OTHER INFORMATION: Description of Artificial Sequence: PCR primer

<400> SEQUENCE: 1
atcggatcct cgaggttttg gcttaggctc                    30

<210> SEQ ID NO 2
<211> LENGTH: 26
<212> TYPE: DNA
<213> ORGANISM: Artificial Sequence
<220> FEATURE:
<223> OTHER INFORMATION: Description of Artificial Sequence: PCR primer

<400> SEQUENCE: 2
atcggatccg gtcggcatct actcta                        26

<210> SEQ ID NO 3
<211> LENGTH: 23
<212> TYPE: DNA
<213> ORGANISM: Artificial Sequence
<220> FEATURE:
<223> OTHER INFORMATION: Description of Artificial Sequence: PCR primer

<400> SEQUENCE: 3
ttgtttgtct ctgccccgtt ttc                           23

<210> SEQ ID NO 4
<211> LENGTH: 25
<212> TYPE: DNA
<213> ORGANISM: Artificial Sequence
<220> FEATURE:
<223> OTHER INFORMATION: Description of Artificial Sequence: PCR primer

<400> SEQUENCE: 4
cgtcgcggtg agttcaggct ttttc                         25